(12) United States Patent
Baldauf et al.

(10) Patent No.: US 11,660,141 B2
(45) Date of Patent: May 30, 2023

(54) PERSONALIZED CORONARY STENTS

(71) Applicant: International Business Machines Corporation, Armonk, NY (US)

(72) Inventors: Julia S. Baldauf, South Melbourne (AU); Darcy J. Beurle, West Melbourne (AU); Matthew Downton, Carlton (AU); Kerry J. Halupka, Brunswick (AU); Stephen M. Moore, Melbourne (AU); Christine Schieber, Southbank (AU)

(73) Assignee: International Business Machines Corporation, Armonk, NY (US)

( * ) Notice: Subject to any disclaimer, the term of this patent is extended or adjusted under 35 U.S.C. 154(b) by 474 days.

(21) Appl. No.: 16/747,060

(22) Filed: Jan. 20, 2020

(65) Prior Publication Data
US 2020/0163720 A1    May 28, 2020

Related U.S. Application Data

(62) Division of application No. 15/651,197, filed on Jul. 17, 2017, now Pat. No. 10,568,696.

(51) Int. Cl.
*A61B 34/10*    (2016.01)
*A61F 2/915*    (2013.01)
(Continued)

(52) U.S. Cl.
CPC .............. *A61B 34/10* (2016.02); *A61F 2/844* (2013.01); *A61F 2/915* (2013.01);
(Continued)

(58) Field of Classification Search
CPC .............. A61B 34/10; A61B 2034/104; A61B 2034/105; A61B 2034/108;
(Continued)

(56) References Cited

U.S. PATENT DOCUMENTS

| 5,554,181 A | 9/1996 | Das |
| 5,658,311 A | 8/1997 | Baden |

(Continued)

FOREIGN PATENT DOCUMENTS

| CN | 102711677 | 10/2012 |
| CN | 104224412 | 12/2014 |

(Continued)

OTHER PUBLICATIONS

China National Intellectual Property Administration, Search Report, CN201880047323.2, dated Apr. 26, 2021, pp. 1-7 (English translation not readily available; significance believed apparent from art listing).

(Continued)

*Primary Examiner* — Jitesh Patel
(74) *Attorney, Agent, or Firm* — Peter Edwards; Otterstedt & Kammer PLLC

(57) ABSTRACT

A method including generating a 3-D model of an unstenosed geometry of a blood vessel responsive to a 3-D model of an actual geometry of the blood vessel, establishing a parametric description of a stent that is expanded from a collapsed configuration to a final configuration that apposes the unstenosed geometry, developing a design for the stent by varying parameters of the parametric description responsive to a design heuristic that includes risk of stent strut breakage during a plastic deformation between the collapsed configuration and the final configuration, embodying the stent according to the design for the stent, inserting the stent into a blood vessel in its collapsed configuration, maneuvering the stent through the blood vessel to a stenosis, and expanding the stent to its final configuration.

8 Claims, 9 Drawing Sheets

(51) Int. Cl.
*A61F 2/844* (2013.01)
*A61B 90/00* (2016.01)
*A61B 34/20* (2016.01)
*A61F 2/958* (2013.01)

(52) U.S. Cl.
CPC ... *A61B 2034/104* (2016.02); *A61B 2034/105* (2016.02); *A61B 2034/108* (2016.02); *A61B 2034/2048* (2016.02); *A61B 2090/3735* (2016.02); *A61B 2090/3966* (2016.02); *A61F 2002/91575* (2013.01); *A61F 2002/9583* (2013.01); *A61F 2240/002* (2013.01)

(58) Field of Classification Search
CPC .... A61B 2034/2048; A61B 2090/3735; A61B 2090/3966; A61F 2/844; A61F 2/915; A61F 2002/91575; A61F 2002/9583; A61F 2240/002
See application file for complete search history.

(56) References Cited

U.S. PATENT DOCUMENTS

| | | | |
|---|---|---|---|
| 5,776,141 | A | 7/1998 | Klein et al. |
| 5,935,135 | A | 8/1999 | Bramfitt et al. |
| 5,938,697 | A | 8/1999 | Killion et al. |
| 6,048,350 | A | 4/2000 | Vrba |
| 6,027,510 | A | 8/2000 | Alt |
| 6,258,099 | B1 | 7/2001 | Mareiro et al. |
| 6,273,910 | B1 | 8/2001 | Limon |
| 6,955,723 | B2 | 10/2005 | Pacetti et al. |
| 7,261,686 | B2 | 8/2007 | Couvillon, Jr. |
| 7,536,042 | B2 | 5/2009 | Murphy et al. |
| 8,042,485 | B1 | 10/2011 | DesNoyer et al. |
| 8,311,312 | B1* | 11/2012 | Richardson .......... G01N 21/952 382/141 |
| 9,195,800 | B2 | 11/2015 | Grady et al. |
| 9,943,627 | B2 | 4/2018 | Zhou et al. |
| 2001/0010012 | A1 | 7/2001 | Edwin et al. |
| 2002/0010489 | A1 | 1/2002 | Grayzel et al. |
| 2002/0068968 | A1* | 6/2002 | Hupp .................. A61F 2/856 623/1.15 |
| 2004/0153128 | A1 | 8/2004 | Suresh et al. |
| 2004/0236398 | A1 | 11/2004 | Burgmeier et al. |
| 2007/0100420 | A1 | 5/2007 | Kavanagh et al. |
| 2007/0118243 | A1 | 5/2007 | Schroeder et al. |
| 2007/0293936 | A1* | 12/2007 | Dobak, III ................ A61F 2/82 623/1.13 |
| 2007/0294280 | A1* | 12/2007 | Jung .................. A61B 1/00082 707/999.102 |
| 2008/0077265 | A1* | 3/2008 | Boyden ................ G06Q 10/087 700/98 |
| 2008/0137923 | A1* | 6/2008 | Spahn ..................... G06T 5/008 382/128 |
| 2010/0017171 | A1 | 1/2010 | Spilker et al. |
| 2010/0228338 | A1 | 9/2010 | Thompson |
| 2011/0066222 | A1* | 3/2011 | Wang ..................... B29C 49/00 623/1.15 |
| 2011/0257673 | A1 | 10/2011 | Heraty et al. |
| 2012/0324696 | A1 | 12/2012 | Liu |
| 2014/0072610 | A1 | 3/2014 | Venkatraman et al. |
| 2014/0088698 | A1 | 3/2014 | Roels et al. |
| 2014/0222184 | A1 | 8/2014 | Verschueren et al. |
| 2015/0051886 | A1 | 2/2015 | Grady et al. |
| 2015/0088240 | A1 | 3/2015 | Lam |
| 2015/0097315 | A1 | 4/2015 | DeSimone et al. |
| 2015/0105852 | A1 | 4/2015 | Noffke et al. |
| 2016/0022208 | A1 | 1/2016 | Gopinath |
| 2016/0256610 | A1 | 9/2016 | Zhou |
| 2016/0310303 | A1 | 10/2016 | Thapliyal |
| 2018/0117219 | A1* | 5/2018 | Yang ........................ A61F 2/82 |
| 2019/0015158 | A1 | 1/2019 | Baldauf et al. |
| 2019/0015159 | A1 | 1/2019 | Baldauf et al. |
| 2020/0390541 | A1* | 12/2020 | Thapliyal .............. A61F 2/2415 |

FOREIGN PATENT DOCUMENTS

| | | |
|---|---|---|
| CN | 104394808 | 3/2015 |
| CN | 105853036 | 8/2016 |
| CN | 105877881 | 8/2016 |
| CN | 106063734 | 11/2016 |
| CN | 106491241 | 3/2017 |
| CN | 106859822 | 6/2017 |
| JP | H9512194 A | 5/1995 |
| JP | 2004528858 A | 9/2004 |
| JP | 2012210456 | 11/2012 |
| WO | 2013050525 A1 | 4/2013 |
| WO | WO2016141215 | 9/2016 |

OTHER PUBLICATIONS

Japanese Patent Application No. 2020-501177, Notice of Reasons for Refusal, English Translation, dated Aug. 16, 2021 4 Pages.
Morton Kern, "Bioabsorbable stents—where are we now?", Cath Lab Digest v. 20(6), http://www.cathlabdigest.com/articles/Bioabsorbable-Stents-%E2%80%93-Where-Are-We-Now, Jun. 2012, pp. 1-4.
C. Rogers et al., "Balloon-artery interactions during stent placement". Circulation research. Mar. 1999. v.84(4), pp. 378-383.
JJ Wentzel et al., "Coronary stent implantation changes 3-D vessel geometry and 3-D shear stress distribution". J. Biomechanics. Oct. 2000. v.33(10), pp. 1287-1295.
JF Ladisa, et al. "Alterations in regional vascular geometry produced by theoretical stent implantation influence distributions of wall shear stress: analysis of a curved coronary artery using 3D computational fluid dynamics modeling". Biomedical Engineering Online. Jun. 2006 v. 5(1) p. 1-11.
Dinesh K. Patel et al., "Highly stretchable and UV curable elastomers for digital light processing based 3D printing", Adv. Mater. Feb. 2017, v. 29, pp. 1-7. (DOI: 10.1002/adma.201606000).
Craig Bonsignore, "Open stent design", Nitinol Devices & Components, Inc. Dec. 2011. pp. 1-93.
Medis Specials, "QAngio(R) XA research edition v1.0", Dec. 2012, pp. 1-2.
Paul J. Otterstedt, List of IBM Patents or Patent Applications Treated as Related, Feb. 11, 2020, pp. 1-2.
Dr. Fritzsche-Henke, German Patent and Trademark Office, Examination office for class A61F, 100-1628 German Patent and Trademark Office Action dated Feb. 3, 2023. pp. 5, related application file No. File No. 11 2018 003 648.0.

* cited by examiner

PERSONALIZED CORONARY STENTS

CROSS-REFERENCE TO RELATED APPLICATIONS

This application is a divisional of U.S. patent application Ser. No. 15/651,197 filed Jul. 17, 2017, the complete disclosure of which is expressly incorporated herein by reference in its entirety for all purposes.

BACKGROUND

The present invention relates to the medical arts, and more specifically, to interventional cardiology.

Cardiovascular disease is one of the largest health problems in the developed world. One of the more serious forms is Coronary Artery Disease (CAD), which typically occurs when part of the smooth, elastic lining inside a coronary artery becomes hardened, stiffened, and swollen with calcium deposits, fatty deposits, and abnormal inflammatory cells, leading to the formation of a plaque and termed atherosclerosis. This plaque can create an obstruction (known as a stenosis) to the normal supply of oxygenated blood to the heart muscle that can cause chest pain (angina), and ultimately can lead to cardiac arrest.

The field of interventional cardiology is a branch of cardiology that deals specifically with catheter-based treatments of structural heart diseases such as CAD. One interventional cardiology procedure is known as Percutaneous Coronary Intervention (PCI). In one mode of PCI, a catheter is inserted into a major systemic artery in either the groin or the arm and steered towards the entrance to the coronary tree at the beginning of the aorta. This catheter takes the form of a thin tube (known as a Judkins catheter) through which a radio-opaque dye may be delivered into the bloodstream, allowing for visualization of the coronary arteries (known as an angiogram) using a special type of X-ray called fluoroscopy. Other techniques for imaging the coronary arteries (e.g., intravascular ultrasound) also can be utilized. If the narrowing (stenosis) is deemed severe enough, a common treatment is the insertion of a stent to restore the artery to its original (unstenosed) diameter. To place a stent, another catheter is threaded through the first, then deeper down to where a coronary artery is narrowed. When the tip is in place, a balloon with the stent crimped around it is inflated. The balloon tip compresses the plaque and expands the stent. Once the plaque is compressed and the stent is in place, the balloon is deflated and withdrawn. The stent stays in the artery, holding it open.

SUMMARY

Principles of the invention provide techniques for generating personalized coronary stents.

In one aspect, an exemplary method includes generating a 3-D model of an unstenosed geometry of a blood vessel responsive to a 3-D model of an actual geometry of the blood vessel. The method further includes establishing a parametric description of a stent that is expanded from a collapsed configuration to a final configuration that apposes the unstenosed geometry; the parametric description includes parameters that characterize struts of the stent. The method further includes developing a design for the stent by varying parameters of the parametric description responsive to a design heuristic that includes risk of stent strut breakage during a plastic deformation between the collapsed configuration and the final configuration. Additionally, the method includes embodying the stent according to the design for the stent.

According to another aspect of the invention, an exemplary apparatus includes a mandrel that has a generally cylindrical hollow membrane for receiving a balloon and that has a plurality of pillars protruding from an outer surface of the membrane, with at least one of the pillars protruding to a different radius than at least one other of the pillars; and a stent supported on the mandrel by contact of the pillars of the mandrel against bridges of the stent.

According to another aspect of the invention, an exemplary method includes inserting into a blood vessel a stent that has an asymmetric collapsed configuration; maneuvering the stent through the blood vessel to a stenosis at a given location of the blood vessel; and expanding the stent from the collapsed configuration to an asymmetric final configuration that corresponds to an asymmetric unstenosed geometry of the given location within the blood vessel.

According to another aspect of the invention, a non-transitory computer readable medium embodies computer executable instructions, which when executed by a computer, cause the computer to facilitate any of the exemplary methods discussed above. In one or more embodiments, the computer executable instructions include instructions for controlling a 3-D printer to embody the stent.

According to another aspect of the invention, an apparatus includes a memory embodying computer executable instructions; and at least one processor, coupled to the memory, and operative by the computer executable instructions to facilitate any of the exemplary methods discussed above.

As used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

One or more embodiments of the invention or elements thereof can be implemented in the form of a computer program product including a computer readable storage medium with computer usable program code for performing the method steps indicated. Furthermore, one or more embodiments of the invention or elements thereof can be implemented in the form of a system (or apparatus) including a memory, and at least one processor that is coupled to the memory and operative to perform exemplary method steps. Yet further, in another aspect, one or more embodiments of the invention or elements thereof can be implemented in the form of means for carrying out one or more of the method steps described herein; the means can include (i) hardware module(s), (ii) software module(s) stored in a computer readable storage medium (or multiple such media) and implemented on a hardware processor, or (iii) a combination of (i) and (ii); any of (i)-(iii) implement the specific techniques set forth herein.

These and other features and advantages of the present invention will become apparent from the following detailed description of illustrative embodiments thereof, which is to be read in connection with the accompanying drawings.

DETAILED DESCRIPTION

Figures 1A, 1B:
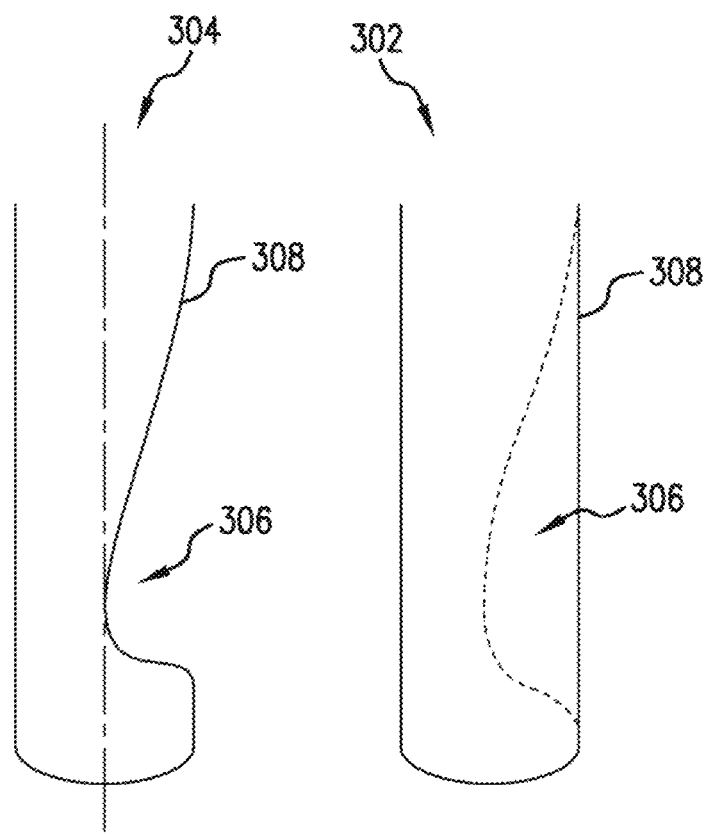
FIG. 1A depicts a 3-D model of a stenosed blood vessel, according to an exemplary embodiment of the invention.
FIG. 1B depicts a desired (unstenosed) vascular geometry developed from the 3-D model of FIG. 1A, according to an exemplary embodiment.

Despite the generally beneficial patient outcomes from PCI, there can be long-term complications such as in-stent restenosis (ISR) or stent thrombosis (ST). ISR occurs when tissue and plaque grow through the stent wall. ST occurs when blood clots adhere to the stent. Either complication results in once again obstructing the normal flow that the stent was supposed to restore.

Advances have been made in stent material selection, so that the current generation of stents include medication-eluting stents (which are coated with a medication that is slowly released to prevent cell proliferation and reduce ISR and ST) as well as bioreabsorbable stents (which are designed to dissolve into the bloodstream over a long period of time that gives the artery opportunity to heal in its unstenosed state). While material selection has a large impact on the patient outcome, another feature of great importance is how well the stent fits within the patient's artery. Ideally when a stent is expanded, it should remain in contact with the arterial wall in an "apposed" state, not pressing into the wall to the point of injuring the endothelium (the layer of cells that form the inner lining of the arterial wall). In this case, the endothelium should form a thin layer that grows over the stent as the artery heals, but not to the point where ISR or ST occur.

Currently stents are manufactured in a range of lengths and diameters and the correct size is chosen from examination of the stenosed artery using an imaging technique e.g. an angiogram. One problem with this approach is that an artery may exhibit tapering or present some complex geometry to which a purely cylindrical structure may not be suitable for maintaining contact with the arterial wall in an apposed state. Thus, differences between off the shelf stent geometry and patient specific geometry can be significant, resulting in complications due to malapposition and incorrect sizing. These differences are in the order of tens to hundreds of microns but currently employed techniques are unable to provide finer control on tolerances. Lack of contact (malapposition) between the stent and the arterial wall can create complex patterns of low wall shear stress (the friction generated by the flowing blood on the arterial wall), resulting in cell proliferation that can lead to ISR and ST.

Based on angiograms or other imaging techniques, it is possible to build a detailed three-dimensional (3-D) model of a blood vessel in its stenosed state. For example, a standard intravascular imaging catheter uses optical coherence tomography, in which radial laser illumination produces high resolution images. By providing an inertial measurement unit ("IMU") in the imaging catheter it is possible to obtain position information. Using the position information, a 3-D model of the blood vessel interior (i.e. the interior of a stenosed blood vessel) can be developed from the images.

In one or more exemplary embodiments, the time varying 3-D model is generated using a camera-equipped catheter that also carries radiopaque position markers. For example, the radiopaque position markers can include a pair of elliptical hoops that are affixed to the catheter such that they remain stationary with respect to the camera. The hoops are disposed orthogonal to one another, and since the entirety of each loop is radiopaque, a full ellipse is visible in an angiogram from all angles, except from an angle parallel to the plane of one of the ellipses, in which case a single line is seen in the angiogram. The camera-equipped catheter is introduced into a patient's vascular system on a guidewire, and camera imagery is captured from the catheter while the catheter is directed through the vascular system to a location of interest for which the 3-D model will be generated. In addition to the camera imagery from the catheter, angiogram imagery of the catheter and guidewire is also captured to define a time varying reference curve, and accelerometer and gyroscope data of the catheter are recorded. By integrating the accelerometer and gyroscope data in time, in combination with the camera imagery and the angiogram imagery, a time varying 3-D model (a 4-D model) of the catheter and of the location of interest is developed. The present disclosure incorporates by reference in their entireties the disclosures of U.S. Pat. No. 10,251,708, entitled "Intravascular Catheter for Modeling Blood Vessels", filed Apr. 26, 2017 and of U.S. patent application Ser. No. 15/498,185, entitled "Intravascular Catheter Including Markers", filed Apr. 26, 2017. However, the precise mode of obtaining the time-varying 3-D model can be varied; for example, a time-varying 3-D model also may be obtained by MRI or by ultrasound. Thus, it is presumed that a time-varying 3-D model is obtained by any method, a stenosis is identified using that model, and the model is smoothed across the region of stenosis to develop an unstenosed geometry.

According to an exemplary embodiment of the present invention, as depicted in FIGS. 1A-1B, a computer generates a 3-D model of an unstenosed geometry 302 of a blood vessel, responsive to a time varying 3-D model of a stenosed geometry 304 of the blood vessel, which is obtained by one of the methods discussed above. In one or more embodiments, the computer averages the time varying 3-D model of the stenosed geometry 304 to identify a stenosis 306, and generates the unstenosed geometry 302 by smoothing a blood vessel wall 308 across the stenosis 306.

Figure 2:
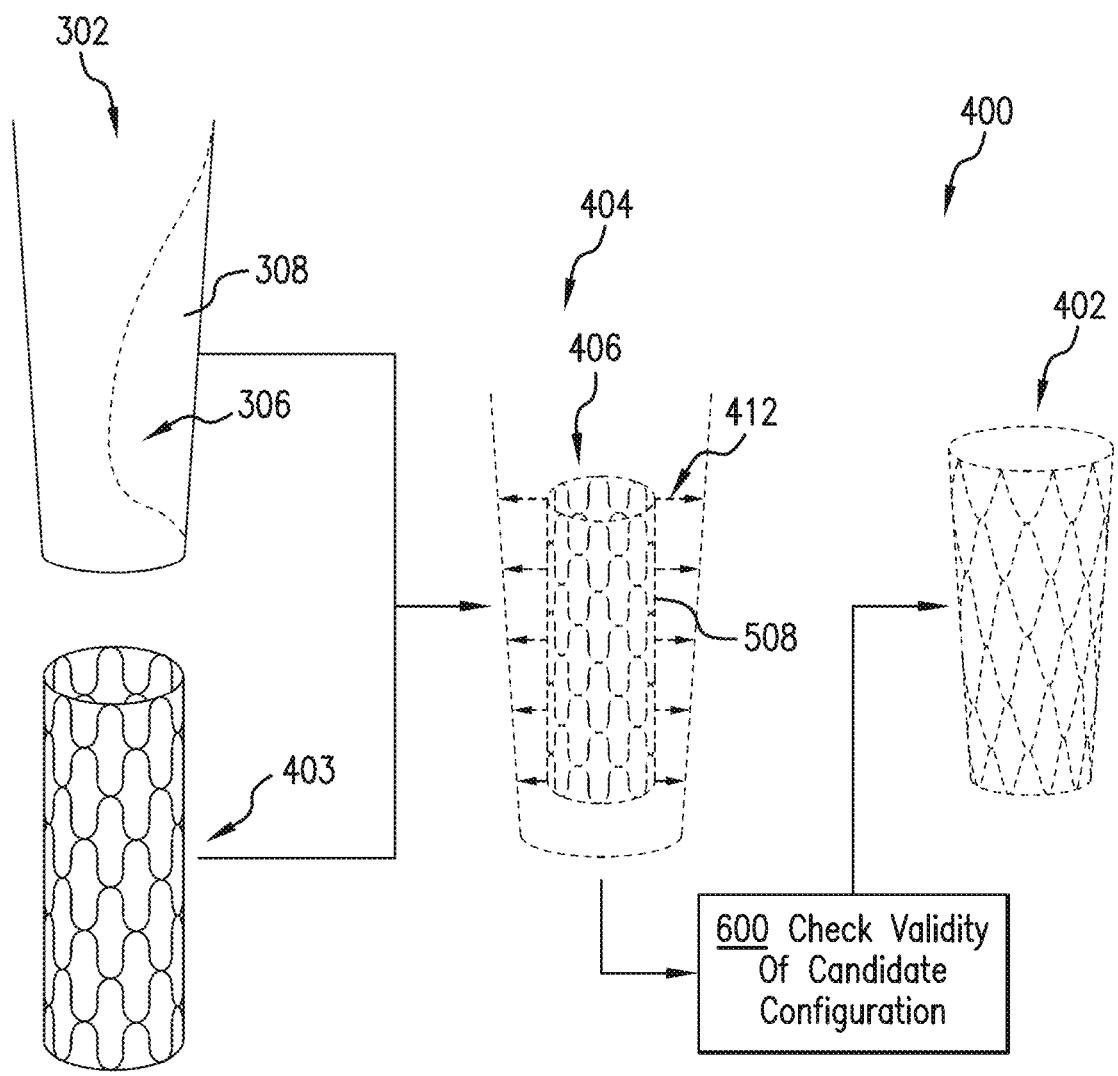
FIG. 2 depicts development of a personalized coronary stent design from a stent template and the desired vascular geometry, according to an exemplary embodiment of the invention.

FIG. 2 depicts in a block diagram a method 400 for developing a final configuration of a personalized coronary stent 402, starting from a generic stent template 403 and the 3-D model of the unstenosed geometry 302. The personalized coronary stent 402, according to embodiments of the invention, properly apposes to the unstenosed geometry 302 and thereby mitigates problems associated with use of off-the-shelf stents.

In order to provide an automated method for generating the final configuration of the personalized coronary stent 402, a parametric description of the stent is necessary. The parametric description defines a few key geometrical parameters that can be tuned in an optimization routine, coupled with a continuum mechanics solver.

Figure 3A:
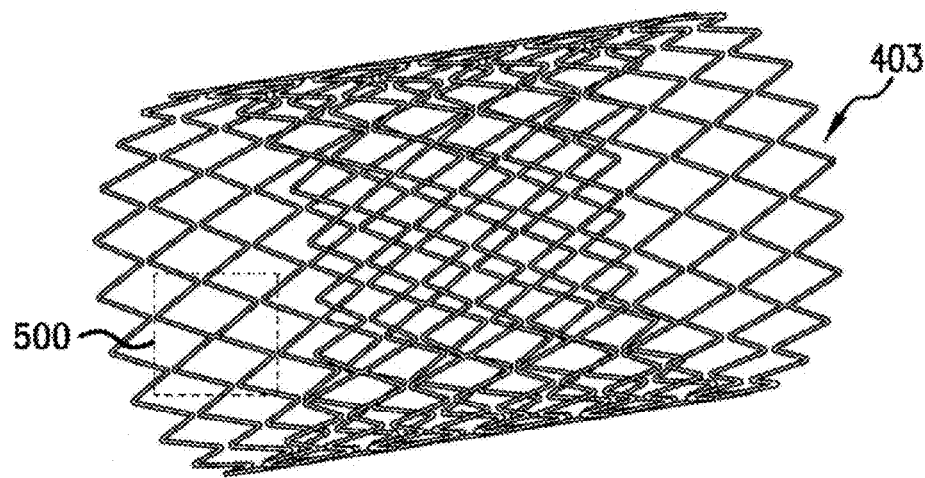
FIG. 3A depicts a parametric design for the generic stent template, according to an exemplary embodiment of the invention.
Figure 3B:
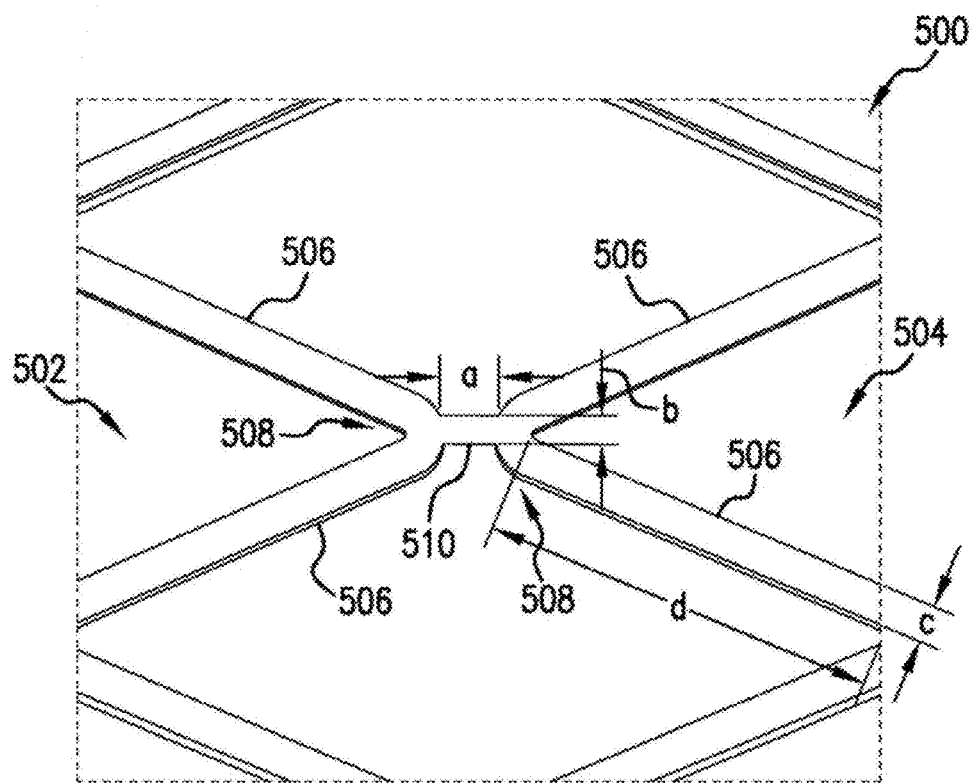
FIG. 3B depicts in a detail view parameters of the parametric design of FIG. 3A.

FIG. 3A depicts the generic stent template 403. FIG. 3B depicts a detailed portion 500 of the generic stent template 403, in which two neighboring arches 502, 504 of the generic stent template 403 are shown. Each arch 502, 504 comprises a pair of struts 506, which join together at a strut junction (an apex 508 of the arch). The apexes 508 of the two arches are connected by a bridge 510. The parameters of this particular design include the length (denoted as a) and the thickness (denoted as b) of the bridge 510, as well as the thickness (denoted as c) and length (denoted by d) of each of the struts 506. As part of determining a final configuration for the patient the software will modify the parameters in the template to ensure that the final configuration of the stent 402 apposes the unstenosed geometry 302 and is not likely to fail during an expansion event.

Referring again to FIG. 2, once the unstenosed geometry 302 has been generated, then the computer implements the method 400 for determining the final configuration of the personalized coronary stent 402 through the use of a design heuristic to adjust key geometric parameters of the generic stent template 403. At 404, the computer generates a candidate configuration 406 by relaxing the apexes 508 of the generic stent template 403 to appose the 3-D model of the unstenosed geometry 302. The computer implements the relaxation by imposing a fictitious radial force 412 on the generic stent template 403, whereby the apexes 508 are evenly distributed onto the unstenosed vascular geometry 302. Next, the computer implements a method 600 (shown in FIG. 4) for checking the validity of the candidate configuration 406 for an installation procedure.

Figure 4:
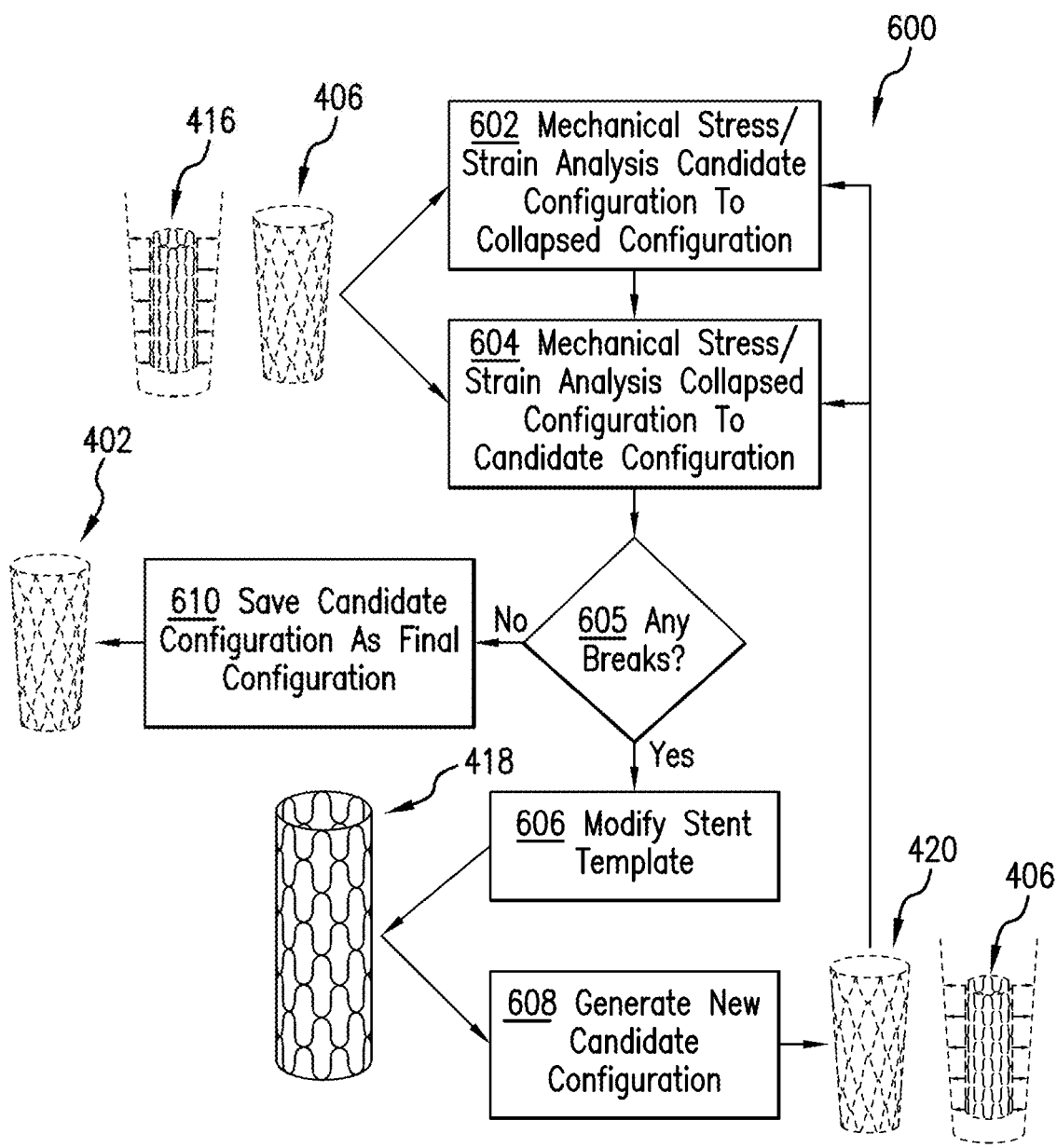
FIG. 4 depicts in a flowchart a method for developing a final configuration of a personalized coronary stent, according to an exemplary embodiment of the invention.

FIG. 4 depicts in a flowchart the method 600 for checking the validity of the candidate configuration 406 for an installation procedure. In one or more embodiments the computer checks the validity of the candidate configuration according to a design heuristic. In one or more embodiments, checking the validity of the candidate configuration 406 includes, at 602, facilitating mechanical stress/strain analysis of a plastic deformation of the stent from the candidate configuration 406 to a collapsed configuration 416 (crimping the stent for insertion into a blood vessel), using the continuum mechanics solver mentioned above. In one or more embodiments, checking the validity of the candidate configuration further includes, at 604, facilitating mechanical stress/strain analysis of a plastic deformation of the stent from the collapsed configuration 416 back to the candidate configuration 406 (expanding the stent for installation in a blood vessel). At 605 the computer applies the design heuristic to the result of the mechanical stress/strain analyses 602, 604. The design heuristic is, for example, no breaks in the stent following the plastic deformations. In case the design heuristic is not met, i.e. the computer identifies any breaks during plastic deformation, then at 606 the computer generates a modified stent template 418, which has different stent strut thicknesses (variable stiffness), by modifying one or more of the parameters a, b, c, d for one or more of the struts 506 and bridges 510 of the generic stent template 403. At 608 the computer generates a new candidate configuration 420, based on the modified stent template 418 and the unstenosed geometry 302.

In one or more embodiments the collapsed configuration 416 matches the modified stent template 418. In other embodiments the collapsed configuration 416 is a version of the candidate configuration 406 that has been plastically deformed (crimped) to fit within the same radius of the modified stent template 418, as further described below with reference to FIG. 9.

The computer repeats blocks 602, 604, 606, 608 until a candidate configuration 406 meets the design heuristic (e.g., no breaks), in response to which the computer facilitates, at 610, saving the valid candidate configuration 406 as the final configuration of the stent 402.

Thus, the method 400 develops a design for the 3-D personalized coronary stent 402 by varying parameters of a parametric description of a generic stent 'template' design 403, wherein the parametric description includes parameters that characterize struts of the stent template. More particularly, the method 400 includes deforming the lengths and thicknesses of the struts 506 and the bridges 510, such that the deformed template can conform to the contours of a complex arterial geometry 302, including features such as tapering, bulges, and other non-axisymmetric features. To modify the stent template 403, the geometry is considered as a simplified structure where the centroids of the apexes 508 define a set of coordinates in 3-D space and line segments defined by two coordinates define a simplified strut or bridge. The points corresponding to the apexes 508 then are iteratively moved around to conform to the complexities of the arterial geometry 302, maintaining topological connectivity of the struts 506 and bridges 510. The way in which the deformation process is performed is that points defining the apexes 508 of the stent struts 506 are iteratively moved radially outward or inward (depending on whether the initial point lies inside or outside of the target geometry surface 302), continuing until all the apexes 508 are within a user specified distance from the surface (an apposition tolerance). The directions to move the points can be computed from either the centerline of the stent template 403 or the centerline of the target geometry 302, or using other common techniques in computational geometry. As discussed above with reference to FIG. 4, the variances of the stent template parameters are repeated responsive to a design heuristic that accounts for or includes a risk of stent strut breakage during a plastic deformation between a collapsed configuration and a final configuration of the stent 402.

Figure 5:
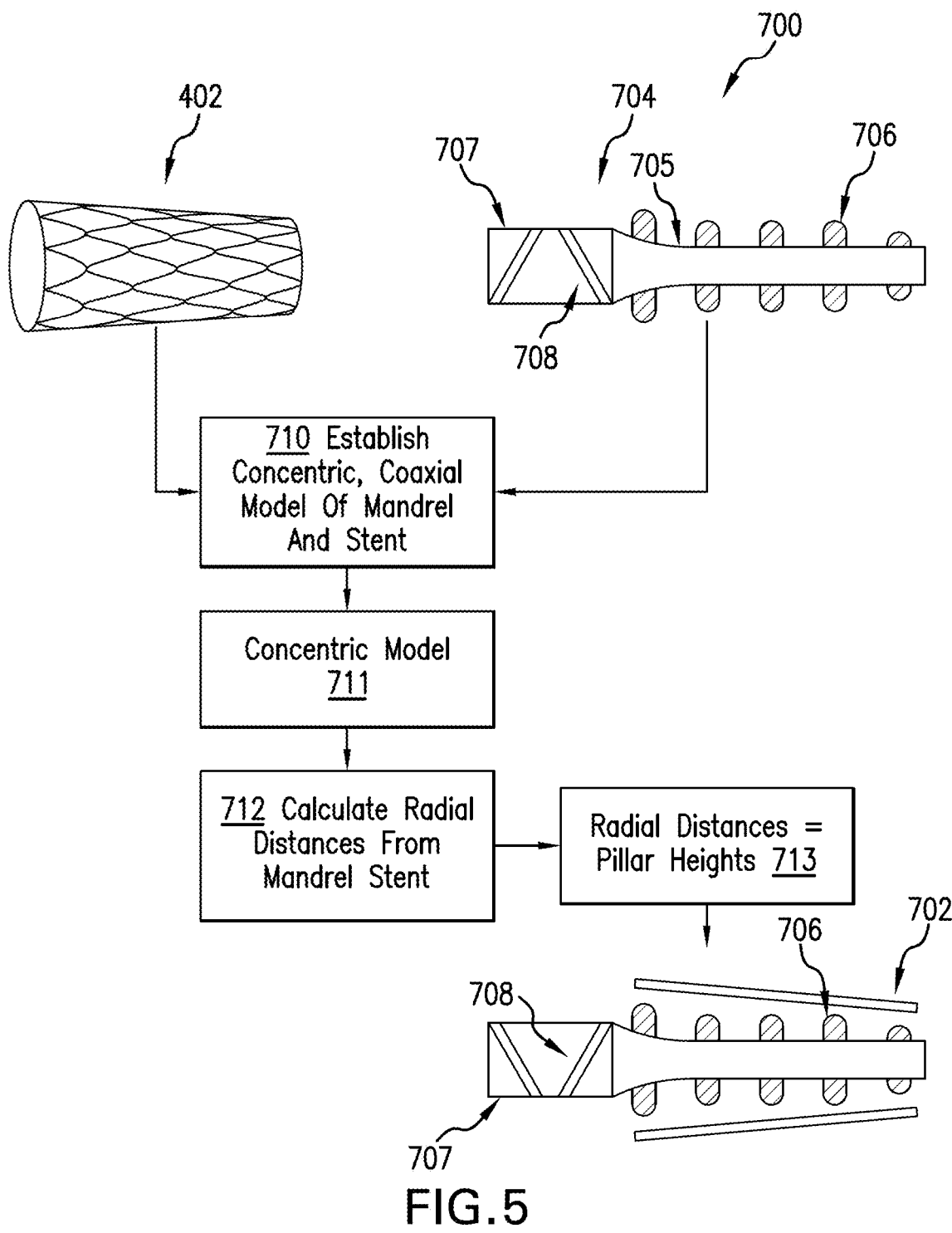
FIG. 5 depicts development of a mandrel geometry from a mandrel template and the personalized coronary stent design, according to an exemplary embodiment of the invention.

FIG. 5 depicts in a flowchart a method 700 for establishing a geometry of a mandrel 702 for supporting the stent 402 in the collapsed configuration. The mandrel 702 is developed from a mandrel template 704 and from the final configuration of the personalized coronary stent 402. The mandrel template 704 has a generally cylindrical body, which for most of its length is formed as a relatively thin membrane 705. The mandrel template 704 also includes a plurality of relatively rigid pillars 706 protruding from the membrane 705, and a relatively rigid guide section 707 that is connected to an end of the membrane 705. In one or more embodiments, the pillars 706 and the guide section 707 can be made relatively rigid by virtue of their thicker cross-sections relative to the membrane 705. The guide section 707 includes radiopaque markers 708, for example, elliptical markers similar to those discussed above with reference to the camera-equipped catheter. The markers 708 are arranged so as to provide univocal indication of the mandrel's position and orientation within an angiogram.

The mandrel 702 has a relaxed geometry and a stretched geometry. In the relaxed geometry the hollow membrane 705 is relaxed and fits over a standard balloon catheter in its uninflated state. In the stretched geometry the hollow membrane 705 is stretched over the standard balloon catheter in its inflated state. The membrane 705 is a relatively flexible membrane, whereas the pillars 706 are relatively rigid members that are attached to the membrane 705 at their bases. The mandrel 702 has each of the plurality of pillars 706 extending to a radius that is determined as follows. First, at 710 establish a model 711 of the mandrel 702 and the personalized coronary stent 402 in a concentric, coaxial configuration. Then at 712 calculate the radial distances 713 from the stretched geometry of the mandrel 702 to each of the bridges 510 of the final configuration of the personalized coronary stent 402. The radial distances 713 will give the heights of the pillars 706. Thus, the positions and sizes of the pillars 706 are chosen to expand the personalized coronary stent 402 from its collapsed configuration 416 to its final configuration, assuming a uniform radial displacement of the mandrel membrane 705 that is provided by inflating the standard balloon catheter.

Figure 6:
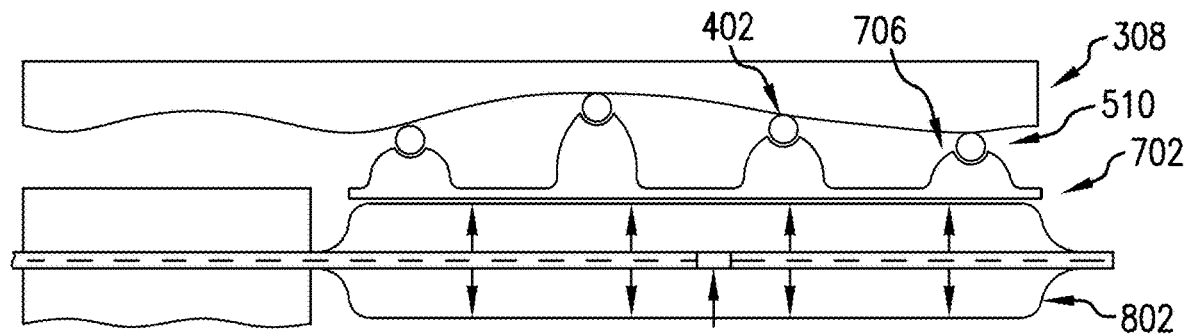
FIG. 6 depicts in a side cross-section view a personalized coronary stent supported on a mandrel within a blood vessel, according to an exemplary embodiment of the invention.

FIG. 6 depicts in a side-cross section view the final configuration of the personalized coronary stent 402, which is supported by its bridges 510 on the pillars 706 of the mandrel 702 within the wall 308 of a blood vessel, according to an exemplary embodiment of the invention. A balloon catheter 802 is shown inflated within the mandrel 702 to hold the mandrel in its stretched geometry. When the balloon catheter 802 is allowed to deflate, the mandrel returns elastically to its relaxed geometry while the personalized coronary stent 402 remains plastically deformed in its final configuration, apposed to the blood vessel wall 308.

Figure 7:
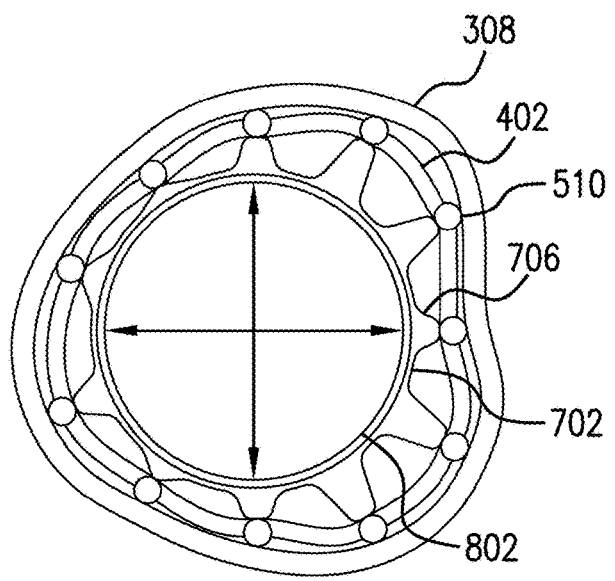
FIG. 7 depicts in an end cross-section view the personalized coronary stent, mandrel, and blood vessel of FIG. 6, according to an exemplary embodiment of the invention.

FIG. 7 depicts the personalized coronary stent 402, the mandrel 702, the balloon catheter 802, and the blood vessel wall 308 in an end cross-section view.

In one or more embodiments, the personalized coronary stent 402 is 3-D printed in its expanded state (final configuration) such that it can be slid over the balloon catheter 802 and mandrel 702 and then plastically crimped down onto them, before deployment. Alternatively, the personalized coronary stent 402 is 3-D printed around the pillars 706 of the mandrel 702, then crimped down onto the pillars 706. This is a main reason why the stent design process includes stress/strain analysis of deformations from the final configuration to the collapsed configuration and back to the final configuration.

Figure 8:
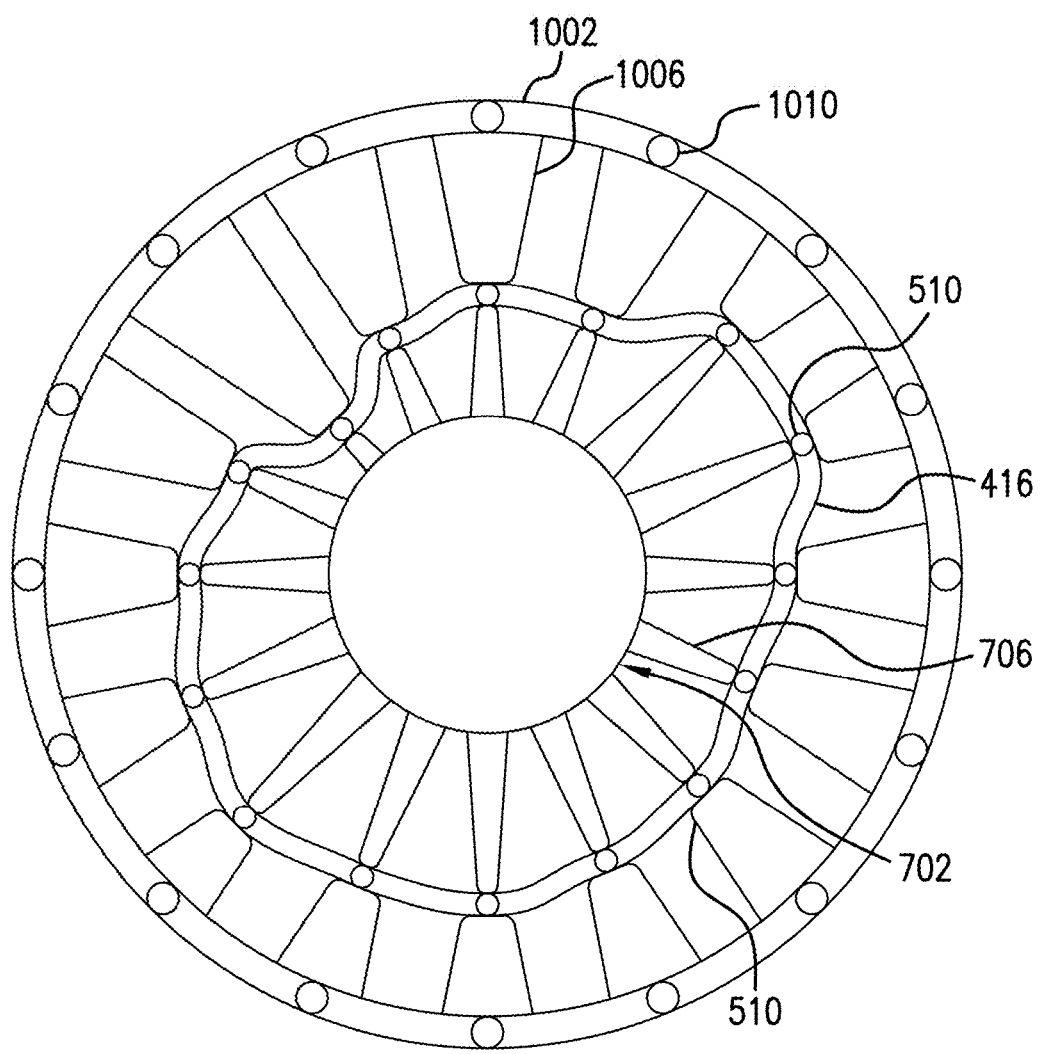
FIG. 8 depicts in an end cross-section view the personalized coronary stent and mandrel of FIGS. 6 and 7, in a crimped configuration, according to an exemplary embodiment of the invention.

Standard crimping devices for coronary stents apply a uniform radial displacement inwards, which would not be feasible for the asymmetric geometry of the personalized coronary stent 402. As such, referring to FIG. 8, a sleeve 1002 is designed and embodied (e.g., 3-D printed) along with the personalized coronary stent 402. The sleeve 1002 allows a standard crimping device to be used for crimping down the stent. The sleeve 1002 has a body 1004 that is essentially the same as the generic stent template, thus, symmetric, but has a slightly larger diameter than the largest diameter of the personalized coronary stent in its final configuration. The sleeve 1002 includes inwardly-protruding fingers 1006, which are blocks of the same 3-D printable material (e.g., polylactic acid) as the rest of the sleeve 1002 and the stent. The fingers 1006 are printed on bridges 1010 of the sleeve 1002, and are aligned in registry with the bridges 510 of the stent, because the bridges do not undergo any circumferential displacement during a crimping or expansion process. The lengths of the fingers 1006 are defined by computing the distance between the support sleeve 1002 and corresponding points of contact (bridges 510) on the stent. Thus, FIG. 8 depicts in an end cross-section view the collapsed configuration 416 of the personalized coronary stent, which has been crimped down onto the pillars 706 of the mandrel 702 by the sleeve 1002.

Figure 9:
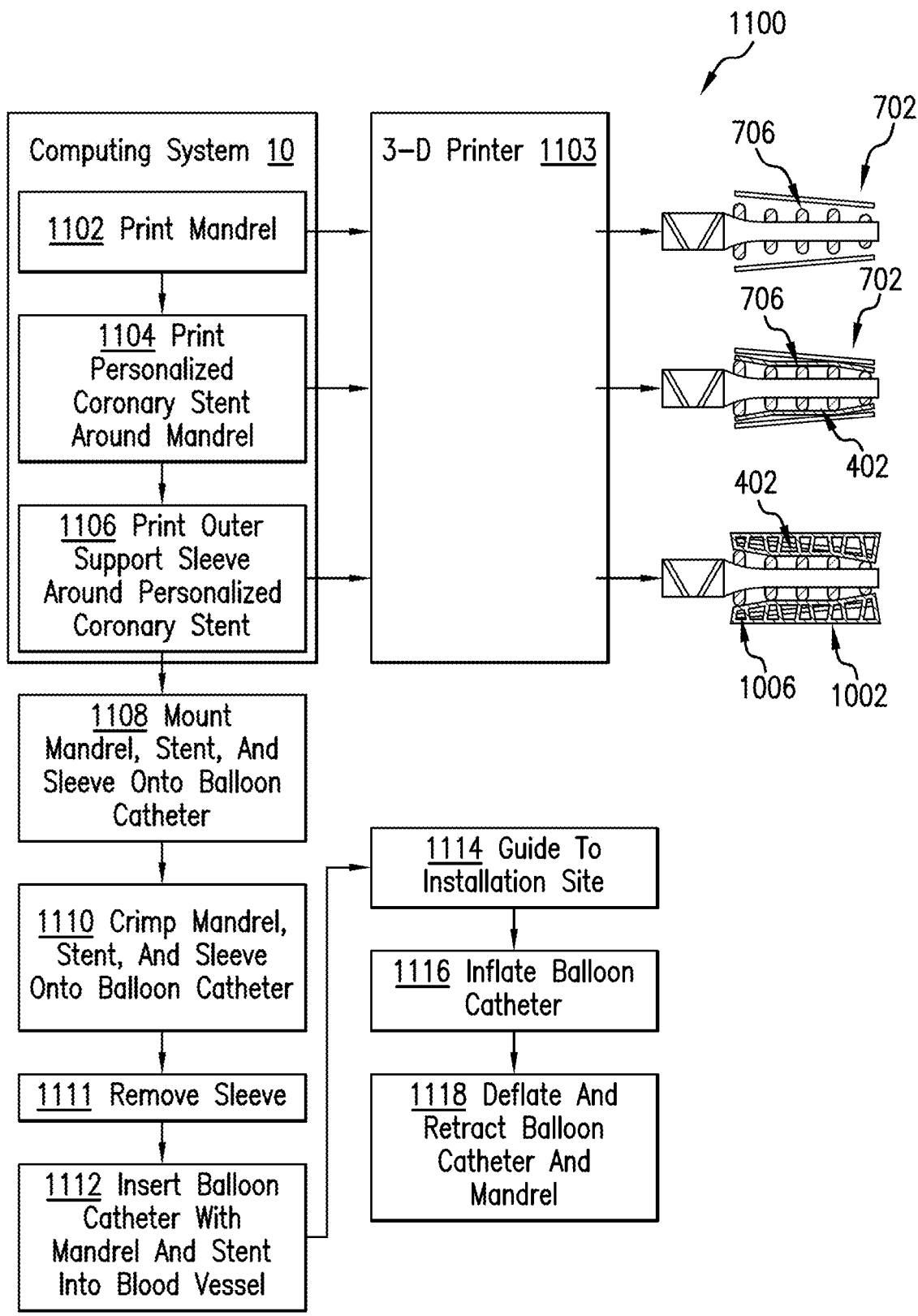
FIG. 9 depicts in a flowchart a method for installing a personalized coronary stent, according to an exemplary embodiment of the invention.

FIG. 9 depicts a method 1100 for building and installing the personalized coronary stent 402, mandrel 702, and sleeve 1002. According to one or more implementations of the method 1100, a computing system 10 facilitates embodying the personalized coronary stent 402 in its final configuration. In one or more embodiments, the computing system 10 facilitates embodying the personalized coronary stent 402 by controlling a 3-D printer 1103. Thus, in one or more embodiments at 1102 the computer controls the 3-D printer 1103 to 3-D print the mandrel membrane 705, the pillars 706, and the guide section 707. For 3-D printing the mandrel 702, a highly flexible but elastic material (e.g., a stretchable UV curable elastomer) is used. Then at 1104 the computer controls the 3-D printer 1103 to 3-D print the personalized coronary stent 402. In one or more embodiments, the personalized coronary stent 402 is printed around the mandrel pillars 706, with the bridges 510 of the stent 402 in registry to the pillars. Responsive to the reference view of the X-ray system to be used during deployment, the elliptical markers 708 can be chosen to have a particular view and this will affect the angular position to which the personalized coronary stent 402 and the pillars 706 are printed onto the mandrel membrane 705 relative to the markers. Alternatively, in one or more embodiments the personalized coronary stent 402 is printed separately from the mandrel 702 and then assembled onto the mandrel. For 3-D printing the stent 402, a plastically deformable material (e.g., polylactic acid) is used.

At 1106 the computer controls the 3-D printer 1103 to print the sleeve 1002 and its fingers 1006. In one or more embodiments, the sleeve 1002 is printed around the personalized coronary stent 402 with the fingers 1006 in registry to the bridges of the stent 402. Alternatively, in one or more embodiments the sleeve 1002 is printed separately from the stent 402 and then assembled onto the stent. For 3-D printing the sleeve 1002, a plastically deformable material (e.g., polylactic acid) is used.

At 1108 the personalized coronary stent 402, the mandrel 702, and the sleeve 1002 are mounted around the balloon catheter 802. At 1110 the assembly is crimped onto the balloon catheter 802. At 1111 the sleeve 1002 is removed, for example, by cutting it off. Then at 1112 the crimped assembly of balloon catheter 802, mandrel 702, and personalized coronary stent 402 is inserted into a blood vessel. At 1114 the assembly is guided to its installation site using continuous or periodic angiograms to validate the assembly position and orientation within the blood vessel. At 1116 the balloon catheter 802 is inflated to plastically deform the personalized coronary stent 402 into apposition with a blood vessel wall 308. At 1118 the balloon catheter 802 is deflated and the catheter and the elastic mandrel 702 are retracted through the blood vessel and out from the insertion site.

A time varying model of the blood vessel can be used to aid in positioning the stent. One could imagine that when the stent is positioned in the artery, it will be moving around due to the motion of the heart and hence coronary arteries. As such, the ellipses on the mandrel will also be moving around and changing their appearance in the angiogram that is acquired while the stent is being positioned. While in one or more embodiments a snapshot of the time varying model is used to create the unstenosed geometry, it is possible to print the mandrel pillars and stent onto the mandrel template such that from a reference viewing angle (for the X-Ray system) and at the point in the cardiac cycle that the snapshot was chosen, one knows that the radiopaque ellipses will appear a certain way in an angiogram frame that matches the corresponding point in the cardiac cycle when the stent is positioned correctly. Furthermore, one will know how the appearance of the ellipses will change as the whole balloon, mandrel, stent assembly moves around during the cardiac cycle, which could provide more information regarding how the assembly is currently positioned.

Techniques of the present invention can provide substantial beneficial technical effects. For example, one or more embodiments provide one or more of:

Improved apposition of stent to lumen wall.

In-laboratory development and fabrication of custom stent designs.

Given the discussion thus far, it will be appreciated that, in general terms, an exemplary method, according to an aspect of the invention, includes generating a 3-D model of an unstenosed geometry of a blood vessel responsive to a 3-D model of an actual geometry of the blood vessel. The method further includes establishing a parametric description of a stent that is expanded from a collapsed configuration to a final configuration that apposes the unstenosed geometry; the parametric description includes parameters that characterize struts of the stent. The method further includes developing a design for the stent by varying parameters of the parametric description responsive to a design heuristic that includes risk of stent strut breakage during a plastic deformation between the collapsed configuration and the final configuration. Additionally, the method includes embodying the stent according to the design for the stent.

In one or more embodiments, the method further includes establishing a geometry of a mandrel for supporting the stent in the collapsed configuration; and embodying the mandrel according to the geometry of the mandrel. In one or more embodiments, establishing the geometry of the mandrel includes establishing a plurality of pillars protruding from a membrane of the mandrel, with at least one of the pillars extending to a different radius than at least one other of the pillars. Additionally, in one or more embodiments establishing the geometry of the mandrel includes configuring the pillars of the mandrel to support bridges of the stent in the collapsed configuration. Also, in one or more embodiments establishing the geometry of the mandrel includes configuring the pillars of the mandrel to also support bridges of the stent in the final configuration, when the mandrel is expanded to its stretched geometry. In one or more embodiments, embodying the mandrel includes 3-D printing the mandrel, and embodying the stent includes 3-D printing the stent around the mandrel with bridges of the stent in registry with the pillars of the mandrel.

In one or more embodiments, embodying the stent includes 3-D printing the stent in the final configuration, and the exemplary method further includes establishing a geometry of a sleeve for facilitating crimping of the stent from the final configuration to the collapsed configuration; and embodying the sleeve according to the geometry of the sleeve. In one or more embodiments, the geometry of the sleeve includes a generally cylindrical body and pillars protruding inwardly from the body. According to certain embodiments, establishing the geometry of the sleeve includes configuring the pillars of the sleeve to uniformly radially compress bridges of the stent from its final configuration to its collapsed configuration. In one or more embodiments, embodying the sleeve includes 3-D printing the sleeve around the stent.

In one or more embodiments, the exemplary method also includes establishing a geometry of a mandrel for supporting the stent in the collapsed configuration; embodying the mandrel according to the geometry of the mandrel; arranging the stent around the mandrel in its final configuration; establishing a geometry of a sleeve for facilitating crimping of the stent from the final configuration to the collapsed configuration; embodying the sleeve according to the geometry of the sleeve; arranging the sleeve around the stent; and crimping the stent onto the mandrel, using the sleeve to distribute a uniform radial force onto asymmetric bridges of the stent.

According to another aspect of the invention, an exemplary apparatus includes a mandrel that has a generally cylindrical hollow membrane for receiving a balloon and that has a plurality of pillars protruding from an outer surface of the membrane, with at least one of the pillars protruding to a different radius than at least one other of the pillars; and a stent supported on the mandrel by contact of the pillars of the mandrel against bridges of the stent.

In one or more embodiments, the apparatus also includes a balloon catheter inserted within the mandrel. In one or more embodiments, the apparatus also includes a sleeve surrounding the stent, the sleeve having inwardly-protruding fingers that contact the bridges of the stent opposing the fingers of the mandrel, with at least one of the inwardly-protruding fingers protruding to a different radius than at least one other of the inwardly-protruding fingers.

In one or more embodiments, a balloon catheter is inserted into the mandrel.

In one or more embodiments, the mandrel includes elliptical radiopaque markers.

According to another aspect of the invention, an exemplary method includes inserting into a blood vessel a stent that has an asymmetric collapsed configuration; maneuvering the stent through the blood vessel to a stenosis at a given location of the blood vessel; and expanding the stent from the collapsed configuration to an asymmetric final configuration that corresponds to an asymmetric unstenosed geometry of the given location within the blood vessel. According to one or more embodiments, the method also includes, during inserting and maneuvering the stent, supporting the stent on a mandrel that has asymmetric pillars for supporting the collapsed configuration of the stent at bridges of the stent, wherein expanding the stent includes inflating a balloon inside the mandrel.

According to another aspect of the invention, a non-transitory computer readable medium embodies computer executable instructions, which when executed by a computer, cause the computer to facilitate any of the exemplary methods discussed above. In one or more embodiments, the computer executable instructions include instructions for controlling a 3-D printer to embody the stent.

According to another aspect of the invention, an apparatus includes a memory embodying computer executable instructions; and at least one processor, coupled to the memory, and operative by the computer executable instructions to facilitate any of the exemplary methods discussed above.

Figure 10:
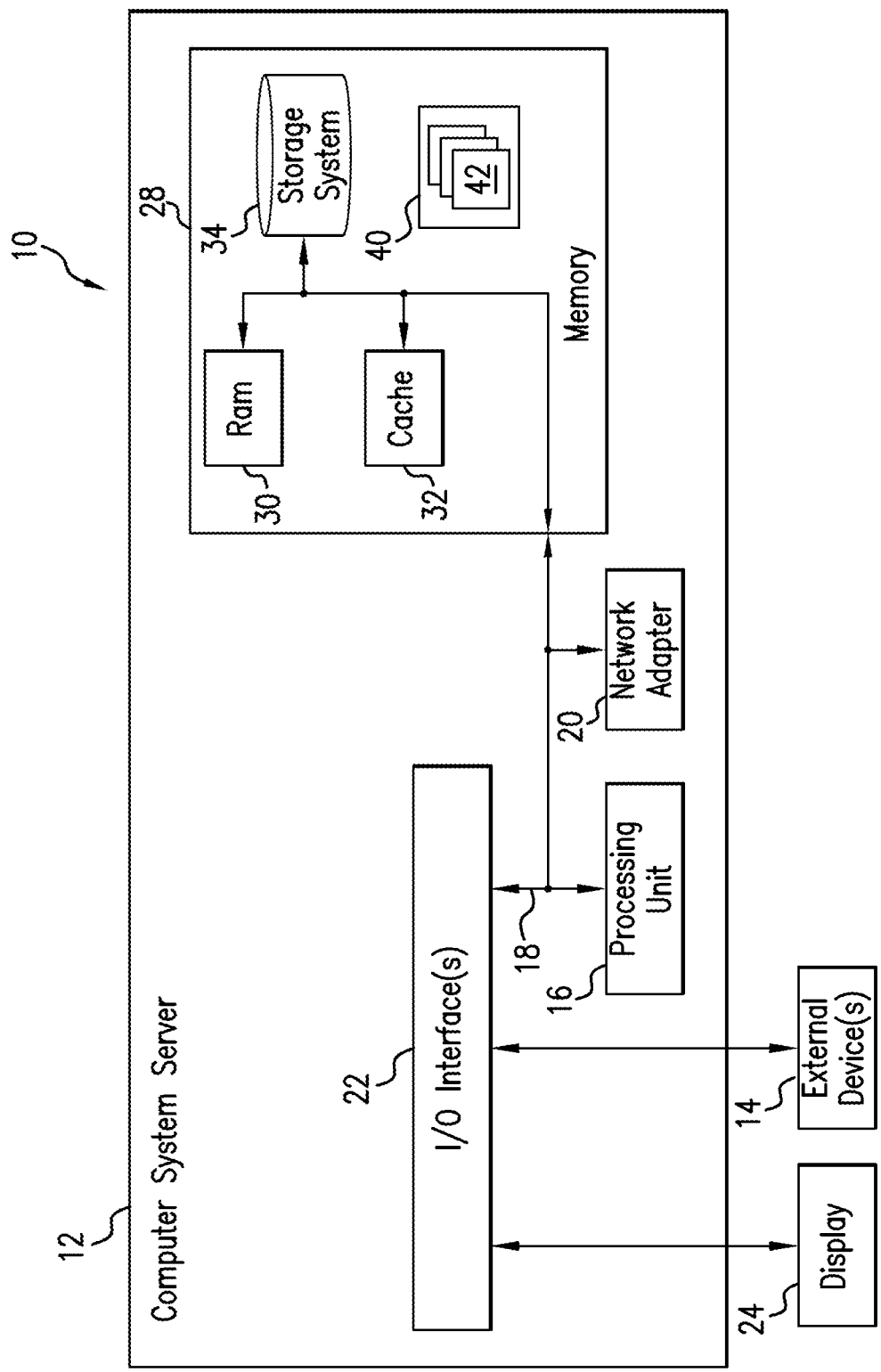
FIG. 10 depicts a computer system that may be useful in implementing one or more aspects and/or elements of the invention, also representative of a cloud computing node according to an embodiment of the present invention.

One or more embodiments of the invention, or elements thereof, can be implemented in the form of an apparatus including a memory and at least one processor that is coupled to the memory and operative to perform exemplary method steps. FIG. 10 depicts an exemplary embodiment of the computing system 10, which may be useful in implementing one or more aspects and/or elements of the invention, also representative of a computer system according to an embodiment of the present invention. Referring now to FIG. 10, computing system 10 is only one example of a suitable computer system and is not intended to suggest any limitation as to the scope of use or functionality of embodiments of the invention described herein. Regardless, computing system 10 is capable of being implemented and/or performing any of the functionality set forth hereinabove.

In computing system 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 10, computer system/server 12 in computing system 10 is in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, and external disk drive arrays, RAID systems, tape drives, and data archival storage systems, etc.

Thus, one or more embodiments can make use of software running on a general purpose computer or workstation. With reference to FIG. 10, such an implementation might employ, for example, a processor 16, a memory 28, and an input/output interface 22 to a display 24 and external device(s) 14 such as a keyboard, a pointing device, or the like. The term "processor" as used herein is intended to include any processing device, such as, for example, one that includes a CPU (central processing unit) and/or other forms of processing circuitry. Further, the term "processor" may refer to more than one individual processor. The term "memory" is intended to include memory associated with a processor or CPU, such as, for example, RAM (random access memory) 30, ROM (read only memory), a fixed memory device (for example, hard drive 34), a removable memory device (for example, diskette), a flash memory and the like. In addition, the phrase "input/output interface" as used herein, is intended to contemplate an interface to, for example, one or more mechanisms for inputting data to the processing unit (for example, mouse), and one or more mechanisms for providing results associated with the processing unit (for example, printer). The processor 16, memory 28, and input/output interface 22 can be interconnected, for example, via bus 18 as part of a data processing unit 12. Suitable interconnections, for example via bus 18, can also be provided to a network interface 20, such as a network card, which can be provided to interface with a computer network, and to a media interface, such as a diskette or CD-ROM drive, which can be provided to interface with suitable media.

Accordingly, computer software including instructions or code for performing the methodologies of the invention, as described herein, may be stored in one or more of the associated memory devices (for example, ROM, fixed or removable memory) and, when ready to be utilized, loaded in part or in whole (for example, into RAM) and implemented by a CPU. Such software could include, but is not limited to, firmware, resident software, microcode, and the like.

A data processing system suitable for storing and/or executing program code will include at least one processor 16 coupled directly or indirectly to memory elements 28 through a system bus 18. The memory elements can include local memory employed during actual implementation of the program code, bulk storage, and cache memories 32 which provide temporary storage of at least some program code in order to reduce the number of times code must be retrieved from bulk storage during implementation.

Input/output or I/O devices (including but not limited to keyboards, displays, pointing devices, and the like) can be coupled to the system either directly or through intervening I/O controllers.

Network adapters 20 may also be coupled to the system to enable the data processing system to become coupled to other data processing systems or remote printers or storage devices through intervening private or public networks. Modems, cable modem and Ethernet cards are just a few of the currently available types of network adapters.

As used herein, including the claims, a "server" includes a physical data processing system (for example, system 12 as shown in FIG. 10) running a server program. It will be understood that such a physical server may or may not include a display and keyboard.

It should be noted that any of the methods described herein can include an additional step of providing a system comprising distinct software modules embodied on a computer readable storage medium; the modules can include, for example, any or all of the appropriate elements depicted in the block diagrams and/or described herein; by way of example and not limitation, any one, some or all of the modules/blocks and or sub-modules/sub-blocks described. The method steps can then be carried out using the distinct software modules and/or sub-modules of the system, as described above, executing on one or more hardware processors such as 16. Further, a computer program product can include a computer-readable storage medium with code adapted to be implemented to carry out one or more method steps described herein, including the provision of the system with the distinct software modules.

Exemplary System and Article of Manufacture Details

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A non-transitory computer readable medium embodying computer executable instructions which when executed by a computer cause the computer to facilitate a method of:
   identifying a stenosis in a three-dimensional (3-D) model of an actual geometry of a blood vessel; and
   generating a 3-D model of an unstenosed geometry of a blood vessel by smoothing the stenosis in the 3-D model of the actual geometry;
   establishing a parametric description of a stent that can be expanded from a collapsed configuration to a final configuration that apposes the unstenosed geometry, wherein the parametric description includes parameters that characterize struts of the stent;
   developing a design for the stent by varying parameters of the parametric description responsive to a design heuristic that includes risk of stent strut breakage during a plastic deformation between the collapsed configuration and the final configuration; and
   embodying the stent according to the design for the stent.

2. The non-transitory computer readable medium of claim 1 wherein the computer executable instructions include instructions for controlling a 3-D printer to embody the stent.

3. The non-transitory computer readable medium of claim 1 wherein the computer executable instructions include instructions for:
   establishing a geometry of a mandrel for supporting the stent in the collapsed configuration; and
   embodying the mandrel according to the geometry of the mandrel.

4. The non-transitory computer readable medium of claim 1 wherein the computer executable instructions include instructions for:
   establishing a geometry of a sleeve for facilitating crimping of the stent from the final configuration to the collapsed configuration; and
   embodying the sleeve according to the geometry of the sleeve.

5. The non-transitory computer readable medium of claim 1, the method further comprising: embodying the stent, without imaging the blood vessel in an unstenosed condition.

6. An apparatus comprising:
   a memory embodying computer executable instructions; and
   at least one processor, coupled to the memory, and operative by the computer executable instructions to facilitate a method of:
   identifying a stenosis in a three-dimensional (3-D) model of an actual geometry of a blood vessel; and
   generating a 3-D model of an unstenosed geometry of a blood vessel by smoothing the stenosis in the 3-D model of the actual geometry;
   establishing a parametric description of a stent that can be expanded from a collapsed configuration to a final configuration that apposes the unstenosed geometry, wherein the parametric description includes parameters that characterize struts of the stent;
   developing a design for the stent by varying parameters of the parametric description responsive to a design heuristic that includes risk of stent strut breakage during a plastic deformation between the collapsed configuration and the final configuration; and
   embodying the stent according to the design for the stent.

7. The apparatus of claim 6 wherein the computer executable instructions include instructions for:
   establishing a geometry of a mandrel for supporting the stent in the collapsed configuration; and
   embodying the mandrel according to the geometry of the mandrel.

8. The apparatus of claim 6 wherein the computer executable instructions include instructions for:

establishing a geometry of a sleeve for facilitating crimping of the stent from the final configuration to the collapsed configuration; and embodying the sleeve according to the geometry of the sleeve.

\* \* \* \* \*